United States Patent [19]

Smith, Jr.

[11] 4,217,353
[45] Aug. 12, 1980

[54] METHOD FOR INDUCING ANOREXIA

[75] Inventor: Dewey H. Smith, Jr., Wilmington, Del.

[73] Assignee: E. I. Du Pont de Nemours and Company, Wilmington, Del.

[21] Appl. No.: 27,270

[22] Filed: Apr. 6, 1979

Related U.S. Application Data

[63] Continuation-in-part of Ser. No. 907,825, May 19, 1978, abandoned.

[51] Int. Cl.² .......................................... A61K 31/485
[52] U.S. Cl. .................................................... 424/260
[58] Field of Search .......................................... 424/260

[56] References Cited

U.S. PATENT DOCUMENTS 3,332,950 7/1967 Blumberg et al. .................. 424/260

OTHER PUBLICATIONS

J. Pharmacol. Exp. Ther. 189, 51–60 (1974) Holtzman.
Life Sciences 16 (9), 1465–1470 (1975) Holtzman.
Chem. Abst. 83 172,541(g) (1975) Holtzman.

*Primary Examiner*—Douglas W. Robinson

[57] ABSTRACT

Naltrexone is administered orally so as to effect appetite suppression in mammals.

3 Claims, No Drawings

METHOD FOR INDUCING ANOREXIA

RELATED APPLICATION

This application is a continuation-in-part of my co-pending application Serial No. 907,825, filed May 19, 1978, now abandoned.

BACKGROUND OF THE INVENTION

This invention relates to inducing anorexia in warm-blooded animals by administering naltrexone orally thereto.

Naltrexone, otherwise known as (−)-17-(cyclopropylmethyl)-4,5α-epoxy-3,14-dihydroxymorphinan-6-one, is known to be a potent narcotic antagonist which shows considerable promise for the treatment of opiate dependence in man. It can be prepared in accordance with the teachings of Blumberg et al. in U.S. Pat. No. 3,322,950, as well as those of Pachter et al. in Canadian Pat. No. 913,077.

Obesity is a serious problem, leading to, among other things, an increased risk of cardiovascular disease. None of the appetite supressants currently available is completely satisfactory.

Holtzman, *J. Pharmacol. Exp. Ther.*, Vol. 189, pages 51–60 (1974), has shown that naloxone (N-allyl-14-hydroxy-7,8-dihydronormorphinone) suppresses eating in food-deprived rats but not in food-deprived mice. In a subsequent study, Holtzman showed that the fluid intake (sweetened Enfamil) of rats was reduced following subcutaneous administration of naloxone, naltrexone or nalorphine (N-allylmorphine); *Life Sciences*, Vol. 16, pages 1465–1470. Having observed in the prior study that the anorexigenic activity of naloxone was species dependent, in the latter study, Holtzman questioned whether naltrexone and nalorphine might show similar species specificity.

The oral route for drug administration is the oldest, and it may be the safest, most convenient, most important, most practical and most economical. However, the fact that a drug causes a certain effect when administered by the parenteral route, e.g. anorexia, does not guarantee that the same effect will be obtained at all when the drug is administered by the oral route. Much less is there any assurance that the same effect will be achieved when the drug is administered orally at a reasonable dosage level. Some drugs may be destroyed by digestive enzymes or low gastric pH. Drugs may form complexes with food which cannot be absorbed. In addition, drugs absorbed from the gastrointestinal tract may be extensively metabolized by the liver before they gain access to the general circulation. In some instances, parenteral administration is essential for the drug to be absorbed in active form. Moreover, there may be other disadvantages to administration of a drug by the oral route; e.g. the gastrointestinal mucosa may become irritated by an orally administered drug and cause emesis.

No study directed to the use of naltrexone as an oral anorexigenic agent has been reported heretofore. However, several studies, directed to the safety and efficacy of naltrexone as an oral narcotic antagonist, contain some isolated and contradictory statements relating to the effect thereof on appetite in man. In all of those studies, the appetite effect was reported by the opiate users themselves; it was not observed by any professional personnel, medical or pharmacological.

Shecter et al., *Proceedings of the National Association for the Prevention of Addiction to Narcotics*, pages 754–765 (1974), report oral administration of naltrexone to 30 male and female subjects, all but 2 of which had been dependent on opiates. One patient, who was receiving 50 mg of naltrexone per day, reported appetite decrease during the naltrexone maintenance period. Another patient, who was receiving a placebo, reported appetite decrease during induction, maintenance, and abrupt withdrawal periods; while yet another patient, who was also receiving a placebo, reported appetite increase during all three such periods. Other patients, who were receiving 125 mg of naltrexone on alternate days of each week, reported both appetite decrease and appetite increase (the number of such patients was not given). No such effect on appetite was reported by the 2 subjects (physicians) having no history of opiate dependence.

Lewis, *American Journal of Drug and Alcohol Abuse*, Vol. 2, (3–4), pages 403–412 (1975), states, in a preliminary report, that the six symptoms most frequently reported by male opiate-addicted patients, following oral naltrexone induction and maintenance, were sweating, yawning, muscle and joint pain, lack of appetite and lack of sexual desire. Except for lack of appetite, all of those symptoms were present also at the same or higher levels prior to naltrexone induction and maintenance. No dosage level information was given by Lewis. Loss of appetite in opiate-addicted patients who are in withdrawal is, of course, no indication of the anorexigenic effect of a drug in non-addicts.

In a study of "street addicts", "methadone maintenance" patients and "post addicts", Bradford et al., *National Institute of Drug Abuse Research*, (1976) Monograph Series 9, one patient out of 45 who was receiving naltrexone, and one patient out of 45 who was receiving a placebo, reported loss of appetite. No dosage information was given.

SUMMARY OF THE INVENTION

A method for exerting an anorexigenic effect in mammals has now been discovered which comprises orally administering to a mammal an effective anorexigenic dose of naltrexone or a pharmaceutically effective salt thereof. Naltrexone exhibits a lower potential for causing side-effects than either amphetamine or fenfluramine, both of which have been used for combatting obesity. In particular, it is neither a stimulant nor a depressant; it does not cause central nervous system excitement, sedation, hypothermia or other side effects.

DETAILED DESCRIPTION OF THE INVENTION

The anorexigenic activity of naltrexone is demonstrated by administering naltrexone to experimental animals and comparing the results with those obtained with a known anorexigenic agent. Naltrexone hydrochloride caused decreased milk-drop consumption in mice, rats and monkeys at lower effective doses than did fenfluramine hydrochloride.

Mouse Anorexia Test

In a quiet room, female white mice, weighing 19–21 g each, which had been fasted for 17–24 hours, were dosed orally with naltrexone.HCl or fenfluramine.HCl salt weight basis in 1.25% Tween 80–1% Methocel - water, at 10 ml/kg mouse. 30 Minutes later, each mouse was transferred to an individual, clear, Lucite ® compartment (13.3 cm ×12.7 cm ×1.27cm) with 0.64 cm ×0.64 cm wire mesh floor. Inside each compartment there was a section of black Lucite ® bar (13 cm ×1.2 cm ×1.2 cm) with 10 spot depressions (0.8 cm diameter) each containing 0.05 ml of 50%-diluted sweetened condensed milk. 30 Minutes later, the number of milk spots consumed was counted. Percent anorexia is calculated based on milk consumption of concurrent vehicle-treated-control mice. The data for concurrently tested naltrexone.HCl and fenfluramine.HCl are given in Table I. ED50%, the effective dose to cause a 50% decrease in milk consumption from control mice, is calculated from a graphical fit of the data.

TABLE I

| Drug | Dose mg/kg | N* | Mouse Consumption Mean No. Drops | Percent Anorexia | ED50% mg/kg |
|---|---|---|---|---|---|
| Naltrexone . HCL | 0 | 40 | 9.80 | — | |
| | 1 | 40 | 8.03 | 18 | |
| | 3 | 40 | 5.98 | 39 | |
| | 9 | 40 | 5.08 | 48 | 8.0 |
| | 27 | 40 | 3.28 | 67 | |
| | 81 | 40 | 1.33 | 86 | |
| Fenfluramine . HCL | 0 | 40 | 9.73 | — | |
| | 2.5 | 40 | 9.75 | 0 | |
| | 5.0 | 40 | 8.93 | 8 | 14.3 |
| | 10.0 | 40 | 6.55 | 33 | |
| | 20.0 | 40 | 3.43 | 65 | |

*N = number of animals tested.

In accordance with the studies summarized in Table I, the ED50% for naltrexone in mice is 8.0 mg/kg as compared to 14.3 mg/kg for fenfluramine hydrochloride.

Rat Anorexia Test

The procedure of the Mouse Anorexia Test was repeated except that the milk drops were placed in depressions in brass bars, 20 drops per rat. The results of the Rat Anorexia Test are set forth in Table II. Pursuant thereto, the ED50% for naltrexone hydrochloride in rats is 3.2 mg/kg as compared to 4.7 mg/kg for fenfluramine hydrochloride.

Table II

| Drug | Dose mg/kg | N* | Rat Consumption Mean No. Drops | Percent Anorexia | ED50% mg/kg |
|---|---|---|---|---|---|
| Naltrexone . HCL | 0 | 20 | 17.70 | — | |
| | 0.75 | 15 | 18.40 | 0 | |
| | 3.0 | 20 | 9.00 | 49 | |
| | 6.0 | 15 | 7.73 | 56 | 3.2 |
| | 12.0 | 20 | 5.50 | 69 | |
| | 24.0 | 15 | 5.40 | 69 | |
| | 48.0 | 20 | 2.15 | 88 | |
| | 96.0 | 15 | 0.60 | 97 | |
| Fenfluramine . HCL | 3 | 20 | 11.80 | 33 | |
| | 6 | 20 | 7.30 | 59 | 4.7 |
| | 12 | 20 | 1.00 | 94 | |

*N = number of animals tested.

Monkey Anorexia Test

Naltrexone and fenfluramine were tested in a side by side dose/time response comparison for anorexia in male Brazilian or Colombian squirrel monkeys. The monkeys (0.9–1.3 kg) were dosed at a minimum interval of seven days using a Latin-square design. They were fasted 16–17 hours prior to dosing. Room temperature was maintained at 25°–26° C.

Tween ® 80 (1 drop/ml 1% Methocel ®) was added to make the stock solutions of the test compounds. There were sonicated, then beadmilled for an hour. The naltrexone doses were 0.0, 0.22, 0.67, 2.0, and 6.0 mg/kg. Fenfluramine was tested at 0, 2.0, 4.0, 8.0, and 16.0 mg/kg. The monkeys were dosed orally with coded doses of the compounds at 2.0 ml/kg.

After the monkeys were weighed and dosed, they were returned to their cages. At 0.5, 1.0, and 2.0 hours after dosing, 30 g of banana-milk in a rubber-stoppered, inverted, glass bottle was suspended from each cage. (Banana-milk is made by mixing 1 can (397 g) of sweetened, condensed milk (Borden's Eagle Brand) and 2 ml of banana creme flavoring (Lorann Oils) in 1000 ml water.) Each drinking interval lasted for 15 minutes. The bottles were weighed before and after each drinking period to determine the amount of banana-milk consumed. The methocel controls generally drank 22–24 g of banana-milk at each drinking interval.

The results of the Monkey Anorexia Test are set forth in Tables III, IV and V. As shown in these tables, the ED50% for naltrexone in monkeys after 0.5 hour was 0.92 mg/kg as compared to 3.3 mg/kg for fenfluramine. After 1.0 hour, the ED50% for naltrexone in monkeys was 0.61 mg/kg versus 1.6 mg/kg for fenfluramine. Finally, at two hours after dosing, the ED50% for naltrexone was 10.7 mg/kg as compared to 2.7 mg/kg for fenfluramine. It is thus seen that, in primates, naltrexone is almost three times as potent an anorexic as fenfluramine at the peak time of one hour. The higher potency of naltrexone at one half hour after dosing also indicates that it exhibits an earlier onset of action than does fenfluramine.

TABLE III

| Monkey Anorexia at 0.5 HR After Dosing | | | | | |
|---|---|---|---|---|---|
| Drug | Dose mg/kg | N* | Mean Grams Consumed | Percent Anorexia | ED50% mg/kg |
| Naltrexone HCL | 0 | 36 | 24.0 | — | |
| | 0.22 | 12 | 21.2 | 12 | |
| | 0.67 | 12 | 13.9 | 42 | 0.92 |
| | 2.0 | 12 | 4.4 | 82 | |
| | 6.0 | 12 | 3.0 | 88 | |
| Fenfluramine HCL | 0 | 36 | 24.0 | — | |
| | 2.0 | 6 | 15.7 | 35 | |
| | 4.0 | 12 | 10.8 | 55 | 3.3 |
| | 8.0 | 12 | 4.8 | 80 | |
| | 16.0 | 6 | 6.2 | 74 | |

*N= number of animals tested.

TABLE IV

| Monkey Anorexia at 1.0 HR After Dosing | | | | | |
|---|---|---|---|---|---|
| Drug | Dose mg/kg | N* | Mean Grams Consumed | Percent Anorexia | ED50% mg/kg |
| Naltrexone HCL | 0 | 36 | 22.7 | — | |
| | 0.22 | 12 | 14.3 | 37 | |
| | 0.67 | 12 | 8.4 | 63 | 0.61 |
| | 2.0 | 12 | 12.3 | 46 | |
| | 6.0 | 12 | 4.9 | 78 | |
| Fenfluramine HCL | 0 | 36 | 22.7 | — | |
| | 2.0 | 6 | 9.3 | 59 | |
| | 4.0 | 12 | 2.2 | 90 | 1.6 |
| | 8.0 | 12 | 2.3 | 90 | |
| | 16.0 | 6 | 0.5 | 98 | |

*N= number of animals tested.

TABLE V

| | | Monkey Anorexia at 2.0 HRS After Dosing | | | |
|---|---|---|---|---|---|
| Drug | Dose mg/kg | N* | Mean Grams Consumed | Percent Anorexia | ED50% mg/kg |
| Naltrexone | 0 | 36 | 21.8 | — | |
| HCL | 0.22 | 12 | 17.8 | 18 | |
| | 0.67 | 12 | 14.6 | 33 | 10.7 |
| | 2.0 | 12 | 13.8 | 37 | |
| | 6.0 | 12 | 12.1 | 44 | |
| Fenflur- | 0 | 36 | 21.8 | — | |
| amine | 2.0 | 6 | 14.3 | 34 | |
| HCL | 4.0 | 12 | 4.8 | 78 | 2.7 |
| | 8.0 | 12 | 3.6 | 83 | |
| | 16.0 | 6 | 0.0 | 100 | |

*N = number of animals tested.

Side Effects

Naltrexone is less toxic orally in mice and has less potential for causing other side effects than either amphetamine or fenfluramine. These characteristics are illustrated by the following tests in mice.

Female white mice, weighing 16–20 g each, which had been fasted for 17–24 hours were dosed orally with naltrexone, amphetamine, or fenfluramine at 0, 4, 12, 36, 108, or 324 mg/kg. The mice were observed at 0.5, 2, 5, and 24 hours after dosing for number of survivors and for signs of mydriasis, ataxia, auditory pinna reflex loss, protection against electroshock, hyperthermia, CNS stimulation (excitement) and tremors.

Mydriasis

Pupillary diameter was measured with a dissecting microscope, the eyepiece of which is fitted with a 100 mm micrometer disc divided into 0.1 mm divisions. A pupillary diameter of 15 divisions (1.5 mm) constituted mydriasis (dilation).

Ataxia

The mouse was placed upright on the benchtop facing away from the observer. Motor incoordination manifested by abnormal gait or lack of precision during purposive movements constituted ataxia.

Auditory Pinna Twitch Reflex

The mouse (front paws) was placed on a bar, 10 to 20 cm horizontally and 9 cm vertically from a Galton whistle adjusted for 13,000 Hertz and with the air escape pointing away from the mouse. If the mouse did not flatten or twitch its ears after 1 or 2 short (0.5 sec) bursts of sound, the pinna reflex was considered lost.

Electroshock Convulsions (EST)

The mice were held by the tail and neck nape and were positioned with the corneas of their eyes touching saline-saturated wick electrodes. A supramaximal (50 ma, 70 volts) alternating current was passed for 0.2 second through the corneal electrodes. Failure of a mouse to extend its hind limbs constituted blockade of the electroshock convulsion.

Hyperthermia

Rectal temperature were taken using a KC-1 thermocouple probe. Temperature more than 2 standard deviations above the mean of 100 vehicle-treated control mice constituted hyperthermia.

Excitement

Increased spontaneous motor activity, running and jumping prior to handling were recorded as excitement (CNS stimuation).

Tremors

All non-convulsive involuntary fine, course, intermittent or continuous movement including fasciculations were recorded as tremors.

The results of the foregoing tests are given in Table VI. This table lists the ED50, in mg/kg, of each drug tested for each symptom observed. The ED50 is the effective dose at which fifty percent of the mice tested exhibited a given symptom. These results clearly indicate that naltrexone is less toxic and has less potential for other side-effects in mice than either amphetamine or fenfluramine, both standard anorectics.

TABLE VI

| | Oral Mouse ED50, mg/kg | | |
|---|---|---|---|
| Drug | Naltrexone | Amphetamine | Fenfluramine |
| Mortality 24 Hr. | 450 | 97 | 232 |
| Mydriasis | none* | 17 | 62 |
| Ataxia | 187 | 1.9 | 3 |
| Auditory Pinna | 450 | 23 | 320 |
| EST | none | 19 | 11 |
| Hyperthermia | none | 19 | none |
| Excitement | none | 3.7 | none |
| Tremors | none | none | 78 |

*none = no effect at top dose.

The dose which would constitute an anorexigenically effective dose in a given mammal would be obvious to one skilled in the art. Based upon the data set forth in the above tables, the human oral dose of naltrexone for use as an anorectic is, according to this invention, 10 to 100 mg per day, preferably 20 mg given 3 or 4 times daily or 60–80 mg total daily dose.

The following provides an example of a suitable dosage form. Equivalent materials and techniques may be used also.

| | |
|---|---|
| Naltrexone hydrochloride | 20 mg/tablet |
| Starch | 65 mg/tablet |
| Lactose | 90 mg/tablet |
| Magnesium stearate | 2 mg/tablet |
| Stearic acid | 5 mg/tablet |

The compound, a portion of the starch, and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid, and the balance of the starch are added and the entire mix blended prior to compression on a suitable tablet press. The tablets are compressed at a weight of 232 mg. using a 11/32 inch punch with a hardness of 4 kg. These tablets will disintegrate within a half hour according to the method described in USP XVI.

What is claimed:

1. A method for exerting an anorexigenic effect in a mammal which comprises orally administering to said mammal an effective anorexigenic amount of naltrexone or a pharmaceutically effective salt thereof.

2. The method of claim 1 wherein said mammal is a human being.

3. The method of claim 2 wherein said effective dose ranges between 10 and 100 mg daily.

* * * * *